United States Patent [19]

Vaughan

[11] Patent Number: 5,599,663
[45] Date of Patent: Feb. 4, 1997

[54] ANGIOTENSIN IV AND ANALOGS AS REGULATORS OF FIBRINOLYSIS

[75] Inventor: Douglas E. Vaughan, Nashville, Tenn.

[73] Assignee: Brighan & Women's Hospital, Boston, Mass.

[21] Appl. No.: 113,292

[22] Filed: Aug. 27, 1993

[51] Int. Cl.$^6$ .......................... C12Q 1/68; G01N 33/567; G01N 33/53
[52] U.S. Cl. .............. 435/6; 435/7.21; 435/7.92
[58] Field of Search ............... 435/6, 7.21, 7.92; 530/316

[56] References Cited

PUBLICATIONS

Gelehrter et al., J. Clin. Invest. 77:165–169, 1986.
Dichek et al., Blood 74:222–228, 1989.
Gavras et al., Lancet 19–22, 1971.
Gavras, H., Hypertension 23:813–818, 1994.
Olson et al., Proc. Natl. Acad. Sci. USA 88:1928–1932, 1991.
Ridker et al., Circulation 87:1969–1973, 1993.
Wright et al., J. Am. Coll. Cardiol. 24:67–73, 1994.
van Leeuwen et al., Circulation 90:362–368, 1994.
Vaughan et al., J. Clin. Invest. 95:995–1001, 1995.
Harding et al., Brain Res. 583:340–343, 1992.
Miller–Wing et al., FASEB 6:3708 Abstract, 1992.
Chaki et al., FASEB 6:3705 Abstract, 1992.
Swanson et al., FASEB 6:3706 Abstract, 1992.
Jarvis et al., Eur. J. Pharm. 219:319–322, 1992.
Sardinia et al., Peptides 15:1399–1406, 1994.
Hall et al., Reg. Peptides 44:225–232, 1993.
Hanesworth et al., J. Pharm. Exptl. Ther. 266:1306–1042, 1993.
Swanson et al., Reg. Peptides 40:409–419, 1992.
Bumpus et al., Biochem. Biophys. Acta 46:38–44, 1961.
Regoli et al., Pharmacol. Reviews 26:69–123, 1974.
Bennett et al., J. Biol. Chem. 251:7423–7430, 1976.
Fitzsimons, J. T., J. Physiol. Lond. 214:295–303.
Tonnaer et al., Brain Res. 236:417–428, 1982.
Siemens et al., Neurochem 57:690–700, 1991.
Kono et al., Acta Endocr. 99:577–584, 1982.
Kono et al., Acta Endocr. 109:249–253, 1985.
Haberl et al., Circ. Res. 68:1621–1627, 1991.
Brazsko et al., Brain Res. 542:49–54, 1991.
Brazsko et al., Neuroscience 27:777–783, 1988.
Brazsko et al., Behav. Brain Res. 25:195–203, 1987.
Semple et al., Circ. Res. 39:671–678, 1976.
Blumberg et al., Circ. Res. 41:154–158, 1977.
Sardinia et al, FASEB, 57(3–4), A437, 1993 (Presented Mar. 28–Apr. 1993).

*Primary Examiner*—Marian C. Knode
*Assistant Examiner*—Patricia A. Duffy
*Attorney, Agent, or Firm*—Fish & Richardson, P.C.

[57] ABSTRACT

Angiotensin IV (VAL-TYR-ILE-HIS-PRO-PHE), a degradation product of angiotensin II previously thought to be inactive, interacts directly with endothelial cells to induce expression of PAI-1 and thereby to inhibit clot lysis attributable to endogenous t-PA. Moreover, angiotensin IV does not effect substantial physiological changes (vasoconstriction, increased blood pressure, etc.) characteristic of angiotensin II. Fibrinolysis is promoted by reducing the amount or the effect of angiotensin IV. Fibrinolysis is inhibited by providing enhanced angiotensin IV. Methods of screening candidates for antagonizing angiotensin IV are also disclosed.

9 Claims, 6 Drawing Sheets

ANGIOTENSIN DEGRADATION SEQUENCE

| PEPTIDE | SEQUENCE | | INHIBITORS |
|---|---|---|---|
| ANGIOTENSIN I | D-R-V-Y-I-H-P-F-H-L | | |
| ↓ | ◄◄◄ ACE | | CAPTOPRIL, ETC. |
| ANGIOTENSIN II | D-R-V-Y-I-H-P-F | | |
| ↓ | ◄◄◄ AMINOPEPTIDASE A | | AMASTATIN, EDTA |
| ANGIOTENSIN III | R-V-Y-I-H-P-F | | |
| ↓ | ◄◄◄ AMINOPEPTIDASE M | | AMASTATIN |
| ANGIOTENSIN IV | V-Y-I-H-P-F | | |

ANGIOTENSIN IV AND ANALOGS AS REGULATORS OF FIBRINOLYSIS

STATEMENT AS TO FEDERALLY SPONSORED RESEARCH

This invention was made at least in part using funding from the United States Government, and the Government has certain rights in the invention.

BACKGROUND OF THE INVENTION

This invention relates to the general field of controlling fibrinolysis.

It is well accepted that most mammals, including humans, have mechanisms that prevent blood loss when a vessel is severed or ruptured. One such mechanism includes a complex cascade of events that culminate in the formation of a blood clot plugging the opening in the vessel in short order after the opening occurs. Once formed, the clot may be invaded by fibroblasts and eventually be organized into fibrous tissue that will permanently close the opening in the vessel. Alternatively, the clot can dissolve.

When a clot is formed, a large amount of a euglobulin plasma protein known as plasminogen is incorporated in the clot along with other plasma proteins. Plasminogen is activated by plasminogen activators which convert plasminogen to plasmin, a proteolytic enzyme that digests fibrin threads and other substances in the surrounding blood, causing lysis of the clot. This process is termed fibrinolysis. A particularly important plasminogen activator, known as tissue plasminogen activator (t-PA), has been well studied as therapeutic to treat acute clotting such as occurs with a myocardial infarction.

The balance between clotting and lysis is affected by plasminogen activator inhibitors, particularly an inhibitor known as PAI-1. Expression of PAI-1 involves the renin-angiotensin system. Specifically, angiotensin II, which is formed by the sequential enzymatic cleavage of angiotensinogen, ultimately results in expression of PAI-1. Olsen et al., Proc. Nat'l. Acad. Sci. U.S.A. (1991) 88:1928–1932. Angiotensin II is also a potent vasoconstrictor. An angiotensin II receptor is known, and blood pressure control therapeutics based on inhibiting formation of angiotensin II (e.g., ACE inhibitors) and based on antagonizing angiotensin (e.g., DUP753) are known.

SUMMARY OF THE INVENTION

I have discovered that angiotensin IV (VAL-TYR-ILE-HIS-PRO-PHE), a degradation product of angiotensin II previously thought to be inactive, interacts directly with endothelial cells to induce expression of PAI-1 and thereby to inhibit clot lysis by t-PA. Moreover, angiotensin IV apparently does not substantially interact with the known angiotensin II receptor, because it does not effect the various physiological changes (vasoconstriction, increased blood pressure, etc.) characteristic of angiotensin II. Further evidence of the direct involvement of angiotensin IV with PAI-1 is found in data showing that the PAI-1-enhancing effect of Angiotensin II is blocked when the conversion of angiotensin II to angiotensin IV is blocked. These findings have application in several aspects of my invention. Broadly, the invention can be divided into aspects featuring promoting fibrinolysis and aspects featuring inhibiting fibrinolysis.

Promoting Fibrinolysis

One aspect of the invention generally features methods of promoting fibrinolysis by administering to a patient an angiotensin IV antagonist, thereby reducing expression of PAI-1. Angiotensin IV antagonists include substances that reduce the effect of angiotensin IV, e.g. by antagonizing (competing with) the binding of angiotensin IV to its receptor, or by directly binding angiotensin IV.

Specific antagonists useful in this aspect of the invention include peptide analogs within the general formula (formula I) given below which: a) inhibit binding of angiotensin IV to a mixture containing an endothelial cell receptor specific for angiotensin IV, and b) do not themselves effect expression of PAI-1. Such analogs may be compounds having the following general formula (or the acetate salts of those compounds):

(Formula I)

A-B-C-HIS-PRO-D (SEQ ID No:1)

where
A=SAR or VAL
B=TYR OR TRP
C=ILE or VAL and
D=ALA or PHE;

provided that if A is VAL and B is TYR and C is ILE, then D is ALA. Specific compounds within that general formula are given below.

Other antagonists include antibodies specific for angiotensin IV, particularly monoclonal antibodies or Fab fragments derived from such antibodies.

A second aspect of the invention generally features methods of promoting fibrinolysis by providing a therapeutically effective amount of a compound which inhibits production of angiotensin IV from angiotensin II. Preferred compounds are inhibitors of aminopeptidase A or aminopeptidase M, such as amastatin.

Medical indications for either of the first two aspects of the invention are those in which the patient has potentially injurious clot formation and fibrinolysis is therefore desired. Specific indications are listed below in this document.

A third aspect of the invention generally features compounds (particularly peptide analogs of angiotensin IV) that antagonize PAI-1 expression by antagonizing binding of angiotensin IV to its receptor. Such compounds include those that fall within the general formula provided above that inhibit binding of angiotensin IV to endothelial cells, and that do not themselves effect expression of PAI-1. Such analogs include the following compounds or the acetate salts thereof:

VAL-TYR-ILE-HIS-PRO-ALA; (SEQ ID NO:2)
SAR-TYR-ILE-HIS-PRO-ALA; (SEQ ID NO:3)
SAR-TYR-VAL-HIS-PRO-ALA; (SEQ ID NO:4)
VAL-TRP-ILE-HIS-PRO-ALA; (SEQ ID NO:5)
VAL-TRP-VAL-HIS-PRO-ALA; (SEQ ID NO:6)
SAR-TRP-VAL-HIS-PRO-ALA; (SEQ ID NO:7)
SAR-TYR-VAL-HIS-PRO-PHE; (SEQ ID NO:8)
SAR-TYR-ILE-HIS-PRO-PHE; (SEQ ID NO:9)
SAR-TRP-VAL-HIS-PRO-PHE; (SEQ ID NO:10) or
SAR-TRP-ILE-HIS-PRO-PHE. (SEQ ID NO:11)

The invention also features physiologically acceptable compositions comprising a therapeutic amount of an angiotensin IV antibody (preferably a monoclonal antibody) or an Fab fragment thereof.

The invention also features physiologically acceptable compositions comprising a therapeutic amount of an inhibitor of aminopeptidase A or aminopeptidase M, such as amastatin.

A fourth aspect of the invention features a method of screening candidate compounds for the ability to promote fibrinolysis by providing a mixture that includes angiotensin IV (or an angiotensin IV receptor-binding analog), an angiotensin IV-specific receptor, and the candidate compound. The screen is conducted by determining whether the candidate inhibits binding of angiotensin IV to the receptor. Candidate compounds include angiotensin IV muteins (e.g., conservative substitutions of angiotensin IV, mutations within the general formula given above, and others) and organic compounds designed therefrom by techniques that are generally known. In addition, such compounds include antibodies (particularly monoclonal antibodies) specific for angiotensin IV, or Fab fragments derived from a such antibodies.

Inhibiting Fibrinolysis

A fifth aspect of the invention generally features methods of inhibiting fibrinolysis in a patient by providing a therapeutically effective amount of angiotensin IV or an agonist thereof. Angiotensin IV may be provided by administering angiotensin IV directly, by administering its immediate precursor, angiotensin III, or by administering or enhancing the activity of enzymes that convert precursors into angiotensin IV. Specific agonists that have application in this aspect of the invention are peptide analogs of angiotensin IV that operate on endothelial cells to bind and enhance PAI-1 expression by the assays described below. This aspect of the invention is specifically indicated for patients who have at least some ability to form clots, but who could benefit from additional clotting. Specific such conditions are listed in this document below.

The invention also features a physiologically acceptable composition comprising a therapeutically effective amount of angiotensin III or IV, or agonists thereof.

Other features and advantages of the invention will be apparent from the following description of the preferred embodiments thereof and from the claims.

DESCRIPTION OF PREFERRED EMBODIMENTS

Embodiments of the aspects of the invention related to enhancing PAI-1 levels and thereby decreasing fibrinolysis will be described separately from embodiments related to reducing PAI-1 levels and thereby increasing fibrinolysis.

I. Promoting Fibrinolysis

The aspect of the invention related to promoting fibrinolysis features decreasing available angiotensin IV or antagonizing the activity of angiotensin IV, e.g. by competitively antagonizing its interaction with an endothelial cell receptor specific for angiotensin IV. Compounds useful for antagonizing angiotensin IV include those which competitively bind to the angiotensin IV receptor by the assay described below, but do not induce PAI-1 expression. Candidate peptide antagonists are discussed above. Specific analogs include the following compounds or the acetate salts of the following:

VAL-TYR-ILE-HIS-PRO-ALA; (SEQ ID NO:2)
SAR-TYR-ILE-HIS-PRO-ALA; (SEQ ID NO:3)
SAR-TYR-VAL-HIS-PRO-ALA; (SEQ ID NO:4)
VAL-TRP-ILE-HIS-PRO-ALA; (SEQ ID NO:5)
VAL-TRP-VAL-HIS-PRO-ALA; (SEQ ID NO:6)
SAR-TRP-VAL-HIS-PRO-ALA; (SEQ ID NO:7)
SAR-TYR-VAL-HIS-PRO-PHE; (SEQ ID NO:8)
SAR-TYR-ILE-HIS-PRO-PHE; (SEQ ID NO:9)
SAR-TRP-VAL-HIS-PRO-PHE; (SEQ ID NO:10) or
SAR-TRP-ILE-HIS-PRO-PHE. (SEQ ID NO:11)

Candidate antagonists can be screened by the general methods described herein. Specific, non-limiting examples of such screens are given below in the Examples.

Clinical indications for treatment with the compounds of the invention include any medical conditions whose treatment would be benefitted by promoting fibrinolysis. These conditions include: a) thromboembolic disorders, b) prophylaxis of undesired clotting as a result of surgery, c) postsurgical maintenance of grafts or prostheses, d) congestive heart failure, e) cardiomyopathy, f) myocardial infarction, and g) cerebrovascular disease. Specific indications include: acute venous thrombosis, pulmonary embolism, atherosclerosis, ventricular or atrial thrombi, peripheral or mesenteric arterial thrombosis, acute coronary infarction or occlusion, and acute peripheral artery occlusion. The compounds may also be administered as prophylaxis against thromboemboli associated with major surgery, congestive heart failure, cardiomyopathy, myocardial infarction, pregnancy, or disseminated intravascular coagulation.

II. Inhibiting Fibrinolysis

The aspects of the invention relating to decreasing fibrinolysis involve enhancing levels of angiotensin IV or agonists thereof. Angiotensin IV may be provided by administering angiotensin IV directly, by administering its immediate precursor, angiotensin III, or by administering or enhancing the activity of enzymes that convert precursors into angiotensin IV.

Specific agonists that have application in this aspect of the invention are peptide analogs of angiotensin IV that operate on endothelial cells to bind and enhance PAI-1 expression. Candidate agonists may be screened for the ability to induce PAI-1 expression by the screens described below.

This aspect of the invention also features administering one or more enzymes that enhance the formation of angiotensin IV by natural pathways. Two such enzymes are aminopeptidase A and aminopeptidase M.

This aspect of the invention is specifically indicated for patients who have at least some ability to form clots, but who could benefit from additional clotting. Specific such conditions include the following:

afibrinogenemia, dysfibrinogenemia, hypoprothrombinemia, parahemophilia, hypoconvertinemia, hemophilia A, hemophilia B, Stuart-Prower factor deficiency, plasma thromboplastin antecedent deficiency, Hageman trait, thrombocytopenia, disorders of platelet function, Von Willebrand's disease, hepatic dysfunction, circulating anticoagulants, inherited defects in natural coagulation inhibitors (such as antithrombin, protein C, or protein S), dysplasminogenemia, defective release or diminished venous content of plasminogen activator, excessive release of PAI, heparin cofactor II deficiency, homocystinuria, chronic congestive heart failure, metastatic tumor or malignancy, extensive trauma or major surgery, myeloproliferative disorders, or treatment with oral contraceptives or L-asparaginase.

III. General Aspects of the Invention

The various peptides described herein may be synthesized by various well known techniques including solid phase synthesis and synthesis by cells engineered to contain recombinant nucleic acid expressing the desired peptide. Angiotensin III or IV and some other peptides also may be purchased from vendors such as Baychem, Torrence, Calif.; Clonetech, Palo Alto, Calif.; Sigma, St. Louis, Mo.

Aminopeptidase A and aminopeptidase M may be obtained by the general methods of Kugler, *Histochemistry* (1982) 74:247–261; Hui, *J. Biol. Chem.* 267:6613–6618;, or from vendors such as Cal Biochem, San Diego, Calif.; or Boheringer Mannheim, Indianapolis, Ind.

Antibodies to angiotensin IV may be obtained by standard techniques involving challenging a mammal (e.g. a mouse, rat, rabbit) with angiotensin IV and recovering polyclonal antibodies from serum or recovering antibody producing cells, immortalizing them and screening for clones producing the desired antibody.

The term "patient" used herein is taken to mean any mammalian patient to which inhibitors or promotors of fibrinolysis may be administered. Patients specifically intended for treatment with the method of the invention include humans, as well as nonhuman primates, sheep, horses, cattle, goats, pigs, dogs, cats, rabbits, guinea pigs, hamsters, gerbils, rats and mice, as well as the organs, tumors, and cells derived or originating from these hosts.

A therapeutically-effective amount of compound is that amount which produces a result or exerts an influence on the particular condition being treated and to be safe and effective in treating the condition of either excess or deficient fibrinolysis for which the compound is administered. Those skilled in the art will understand that dosages can be optimized for a given medical indication and a given therapeutic by standard techniques such as establishing a dosage in an animal model, predicting a subtherapeutic dose for humans, testing safety in humans by increasing that subtherapeutic dose, and then optimizing the therapeutic dose.

The compounds of the invention may be administered in any manner which is medically acceptable. This may include injections, by parenteral routes such as intravascular, intravenous, intra-arterial, subcutaneous, intramuscular, intratumor, intraperitoneal, intraventricular, intraepidural, or others, as well as oral, nasal, ophthalmic, rectal, topical, or as an inhalant preparation. Sustained release administration is also specifically included in the invention, by such means as depot injections or erodible implants. The compounds may also be directly applied during surgery.

It should be understood, however, that the foregoing description of the invention is intended merely to be illustrative by way of example only and that other modifications, embodiments, and equivalents may be apparent to those skilled in the art without departing from its spirit. The following experiments are recited to illustrate the invention, not to limit it. Examples I and II relate to studies of the binding of angiotensin II (AngII) and of the effect of such binding on endothelial cells. Examples 3 and 4 relate to identification of the moiety responsible for inducing expression of PAI-1.

Experiments

Example I—Characterization of the binding of angiotensin II to cultured endothelial cells.

Figure 1:
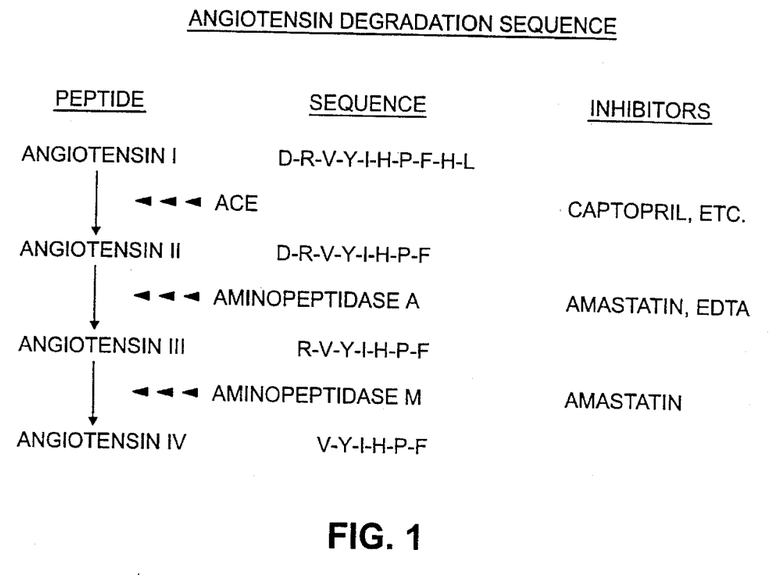
FIG. 1 is a diagram showing the degradation sequence of the peptides angiotensin I, II, III, and IV, as well as the peptides' sequences and inhibitors of the degratory enzymes.
Figure 2:
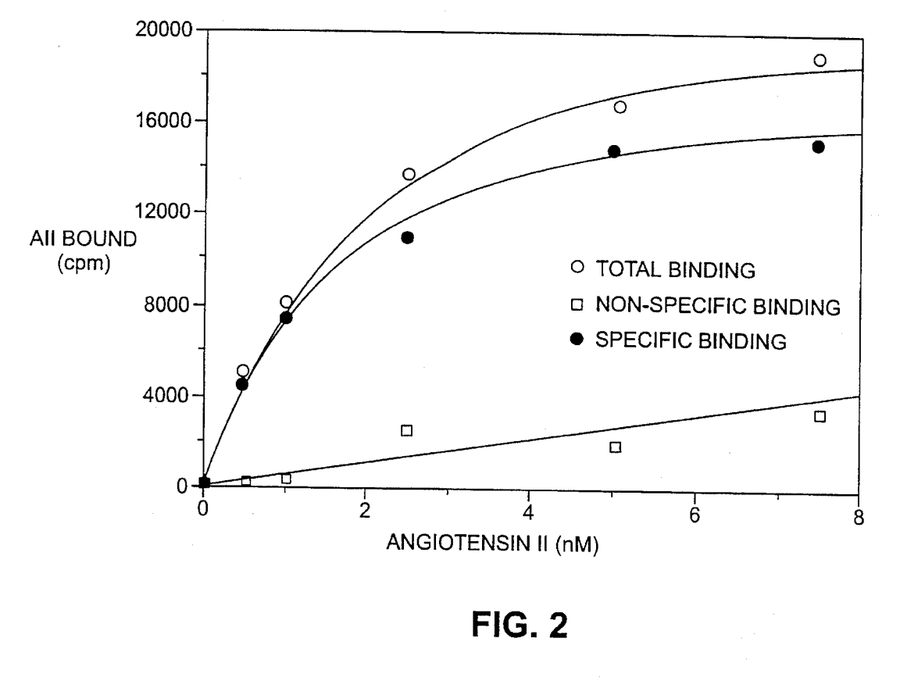
FIG. 2 is a plot showing the binding of $^{125}$I-Ang II to bovine aortic endothelial cells at room temperature, with total, non-specific and specific binding isotherms shown.
Figure 3:
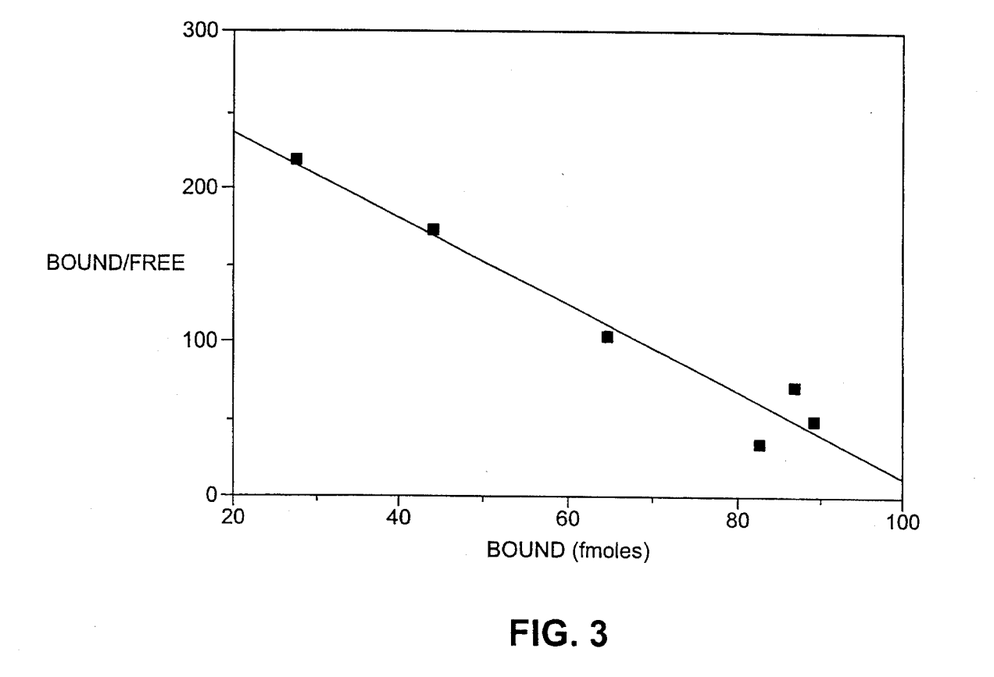
FIG. 3 is a Scatchard plot of specific binding data, yielding a $D_d$ of approximately 2 nM.

We first studied the role of angiotensin (Ang) II in the regulation of endothelial fibrinolysis, by determining if Ang II binds to the target cell, which in this case was bovine aortic endothelial cells. In these experiments, we used early passage bovine aortic endothelial cells (P2–4) grown to confluence in DMEM supplemented with penicillin, streptomycin, and 10% newborn calf serum. When these experiments are performed at room temperature, we have found that binding equilibrium occurs by 45 min. Further, the binding characteristics of cells>passage 5 is highly variable. As shown in FIG. 2, $^{125}$I-Ang II appears to bind to bovine aortic endothelial cells in a saturable and specific manner. A Scatchard transformation of the specific binding data (FIG. 3) yields an apparent $K_d$ of ~2 nM, with $B_{max}=105$ fmol/$10^6$ cells.

Figure 4:
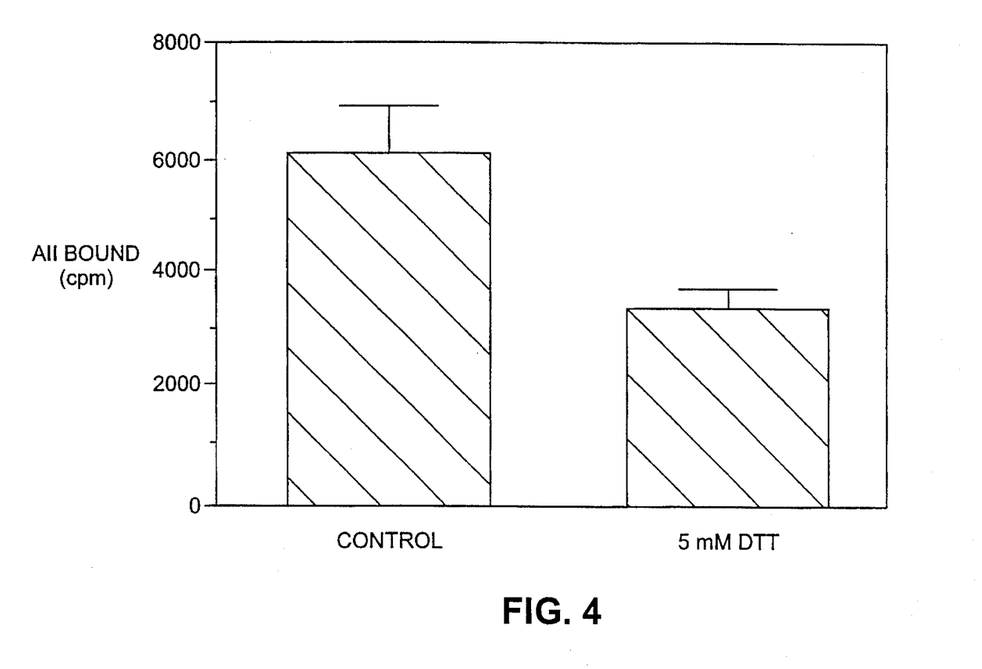
FIG. 4 is a graph showing the effect of DTT on $^{125}$I-Ang II (0.27 nM) to bovine aortic endothelial cells. Values represent the means ±SD of one experiment performed in triplicate.
Figure 5:
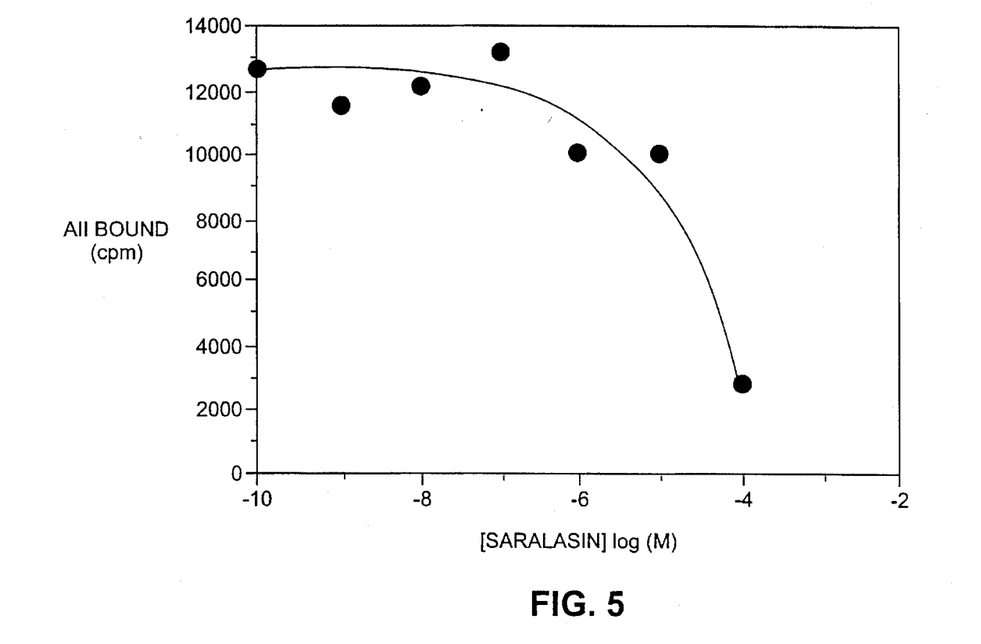
FIG. 5 is a plot showing the effect of saralasin (Sar$^1$,Val$^5$, Ala$^8$)-angiotensin on $^{125}$I-AngII (0.5 nM) binding to bovine aortic endothelial cells. Values represent averages obtained from two experiments.

We further showed that the endothelial angiotensin receptor differs from the classic $AT_1$ receptor in several important ways. After exposing bovine aortic endothelial cells to 5 mM DTT, we observed a 50% reduction in total binding (FIG. 4). This suggests that the bovine aortic endothelial cells receptor for Ang II is somewhat less sensitive to the effects of reducing agents that the classic $AT_1$ receptor. To test whether the Ang II receptor on the bovine aortic endothelial cells is similar or identical to the classic $AT_1$ receptor, we measured the potency of the antagonist saralasin for binding. It is a well established property of the $AT_1$ receptor that the antagonist saralasin binds with a $K_i=0.4$ nM. We performed an experiment in which unlabeled saralasin was used to displace $^{125}$I-AngII from bovine aortic endothelial cells and found an $IC_{50}$ @10 μM (FIG. 5). The failure of saralasin to compete effectively for binding to bovine aortic endothelial cells provides additional evidence that the receptor we are dealing with is not a classic $AT_1$, and in this aspect it appears quite similar to the binding site for Ang IV.

Example 2—Ang II induces the production and secretion of PAI-1 by bovine aortic endothelial cells.

Figure 6:
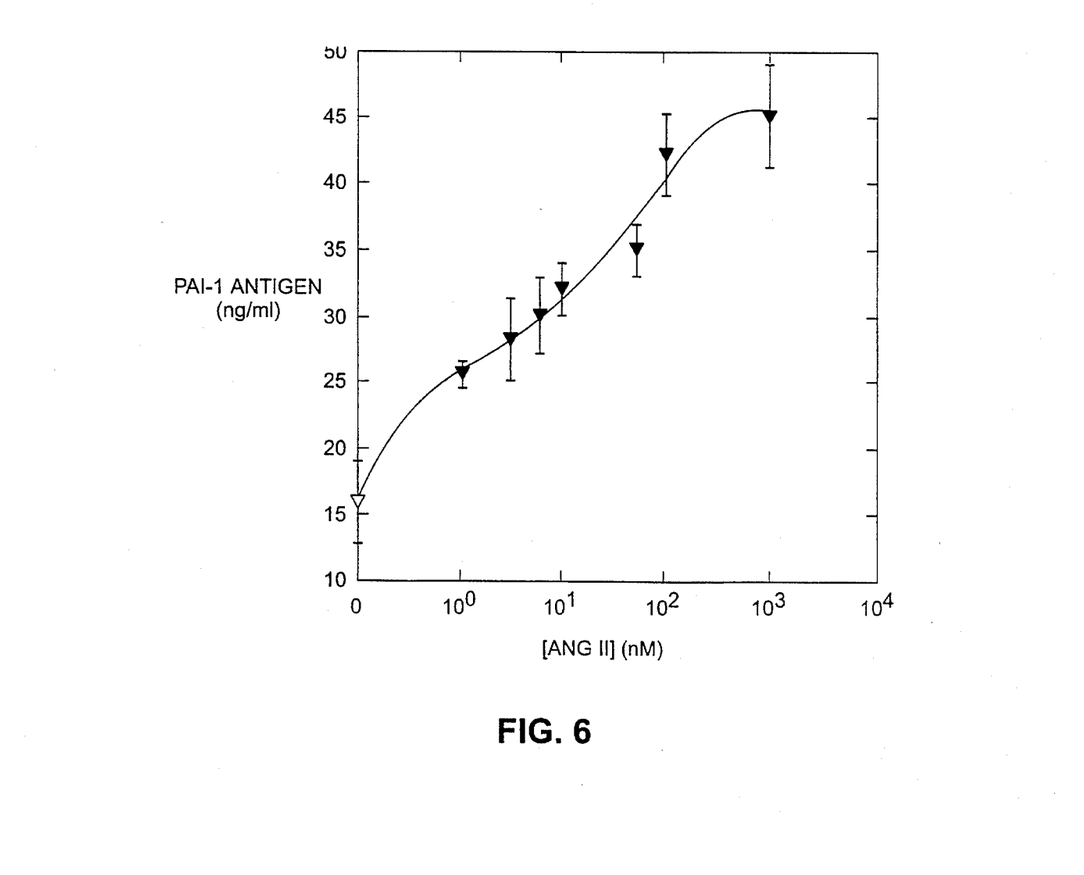
FIG. 6 is a dose response curve of PAI-1 secretion into the conditioned media of bovine aortic endothelial cells following exposure to Ang II.

In these experiments, we investigated the effects of Ang II on the secretion of PAI-1 into the media of cultured endothelial cells. Exposure of bovine aortic endothelial cells to Ang II appears to induce the secretion of PAI-1 in a dose-dependent manner, as shown in FIG. 6. Ang II (in the concentrations indicated) was added to washed, confluent cultures of bovine aortic endothelial cells, and the conditioned media was removed for assay after 18 hour. Levels of PAI-1 antigen in the media were determined using a specific ELISA for PAI-1, such as the assay described in DeClerk et al., *Blood* (1988) 71:220–225, or the assay sold by Biopool, AB, Umea, Sweden.

Figure 7:
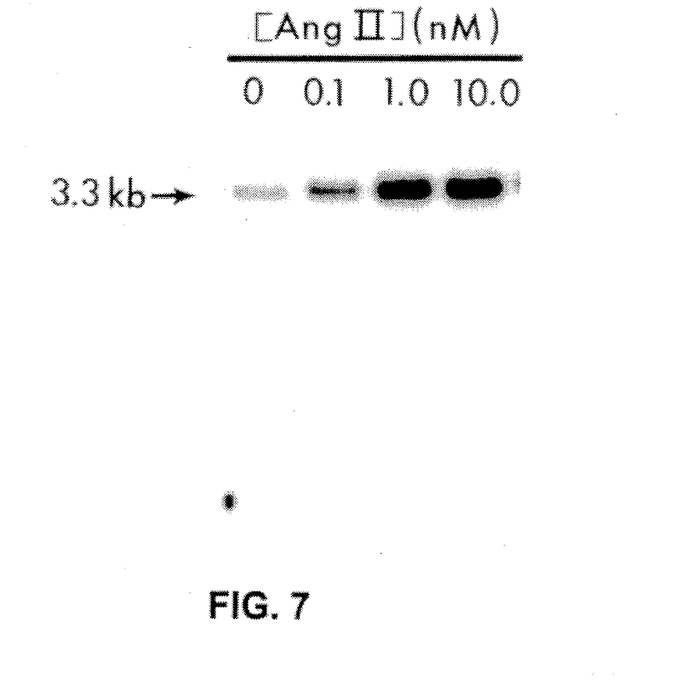
FIG. 7 is a Northern blot showing the induction of PAI-1 RNA after treatment of bovine aortic endothelial cells with angiotensin II.
Figure 8:
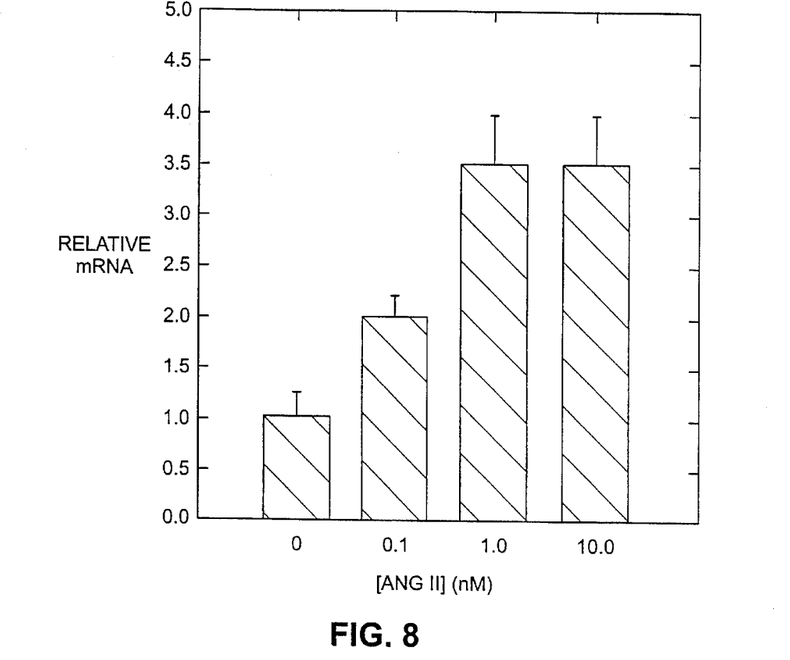
FIG. 8 is a graph showing the dose response of PAI-1 RNA induction by Ang II.

The $EC_{50}$ for this response is ~20 nM, and corresponding changes in PAI-1 activity (after reactivation of the latent protein with guanidine hydrochloride) have also been observed. This effect of Ang II on PAI-1 appears to be specific, as we have not observed a similar increase in t-PA antigen or activity in the conditioned media. The increases in PAI-1 activity and antigen observed thus far have been associated with an approximate 4-fold increase in PAI-1 message (FIGS. 7 and 8). The cells for these experiments were incubated for 8 hour in fresh serum-free media containing the indicated concentrations of Ang II. Total RNA was extracted and analyzed by Northern blotting. FIG. 8 shows levels of PAI-1 mRNA as quantitated by slot/blot analysis in triplicate and normalized for signal intensity of control probe for β-actin. This stimulatory effect of Ang II on PAI-1 mRNA levels does not appear to be prevented by Dup 753 (1 μM) or by saralasin (1 μM).

Figure 9:
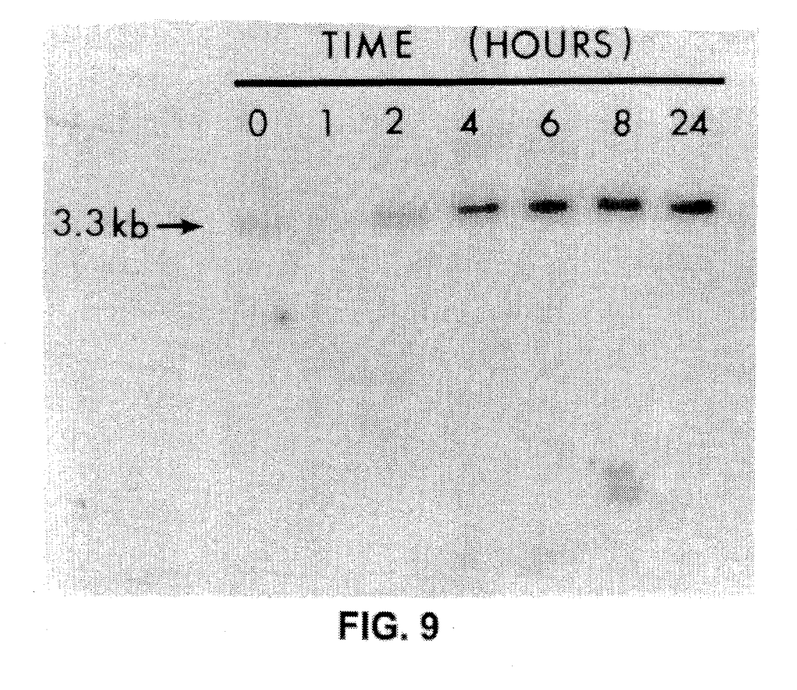
FIG. 9 is a Northern blot showing the time course of induction of PAI-1 RNA after treatment of bovine aortic endothelial cells with 20 nM angiotensin II.
Figure 10:
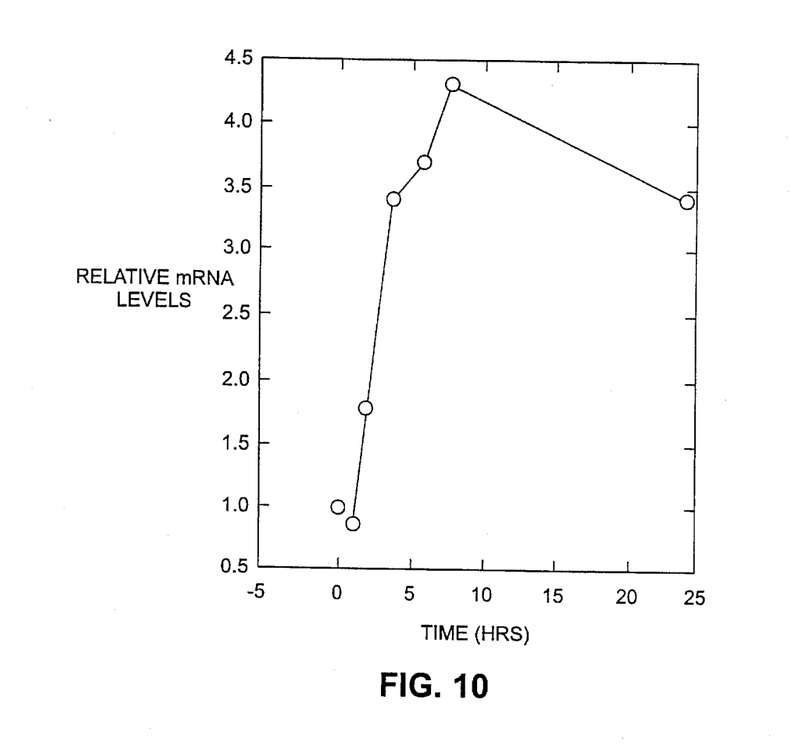
FIG. 10 is a graph showing the PAI-1 mRNA levels as a function of time, in bovine aortic endothelial cells treated with 20 nM angiotensin II.

Ang II is also associated with a time-dependent increase in PAI-1 mRNA that peaks 6–8 hrs after exposure to Ang II, as assessed by Northern blot analysis (FIG. 9). Confluent cultures of bovine aortic endothelial cells were incubated with 20 nM Ang II in serum-free DMEM. Total cytoplasmic RNA was extracted at the indicated times and analyzed by Northern blotting (FIG. 9). The results corresponding to the 3.3-kb PAI-1 mRNA species were quantified by transmission densitometry. To control for variability in gel loading, the blots were stripped and rehybridized with a cDNA probe for β-actin. Normalized data are plotted in the FIG. 10.

In the experiments described above we have first demonstrated that Ang II binds to bovine aortic endothelial cells in a specific and saturable manner. Second, this binding appears to have a functional effect on bovine aortic endothelial cells in inducing the synthesis of PAI-1 message and the secretion of PAI-1 into the conditioned media. Importantly, we have observed increased levels of PAI-1 mRNA induced by physiologically relevant doses of Ang II (i.e. 0.1 nM). The potential significance of these in vitro findings are supported by recent data obtained during the infusion of Ang II into healthy human volunteers. In these studies, normotensive volunteers (N=4) received an infusion of Ang II in graded doses of 1.0, 3.0. and 10.0 ng/kg/min., while 4 additional normotensive volunteers received an infusion of D5W. Plasma levels of t-PA and PAI-1 were measured prior to and at the conclusion of each dose. Plasma PAI-1 levels increased in the subjects that received the Ang II infusions in a dose-dependent manner, from 14.7±5.3 to 33.5±10.6, (mean values±SEM, p<0.001 by ANOVA). Similar findings have been obtained in an additional group of hypertensive volunteers (N=6) that received a constant infusion of Ang II (3 ng/kg/min) over a 45 min period. In these individuals, we observed a 60% increase in plasma PAI-1 compared with pretreatment levels (p<0.04).

These data indicate that Ang II selectively increases levels of PAI-1 in plasma, while plasma t-PA levels do not increase.

Example 4—Identification of agent responsible for enhancing PAI-1

Figure 11:
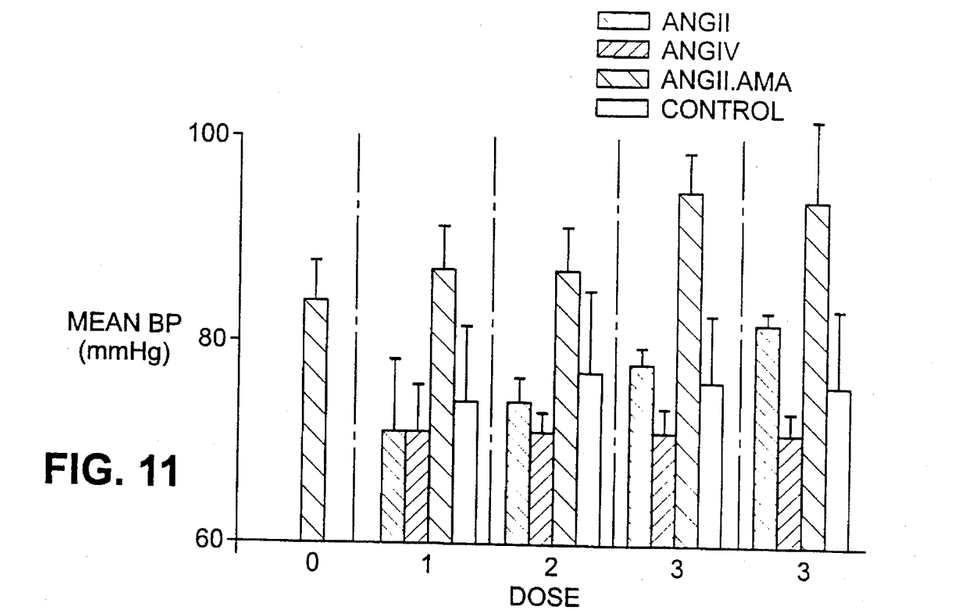
FIG. 11 is a graph of the mean BP at baseline and after increasing doses of Ang II alone, Ang IV alone, saline, and Ang II in rabbits pretreated with amastatin. Error bars represent SEM.
Figure 12:
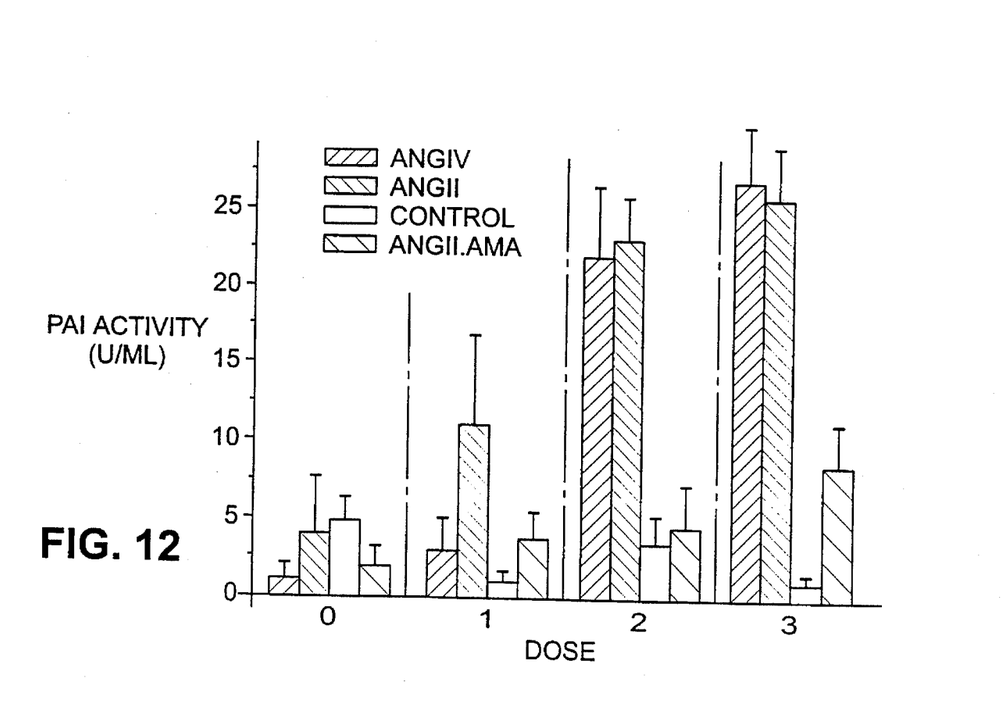
FIG. 12 is a graph of the mean plasma PAI-1 activity at baseline and after increasing doses of Ang II alone, Ang IV alone, saline, and Ang II in rabbits pretreated with amastatin. Error bars represent SEM.

We have also undertaken a series of experiments designed to identify the specific form of angiotensin that is responsible for the increased plasma PAI-1 levels seen in our human studies. We examined the effects of graded infusions of Ang II and Ang IV on blood pressure and plasma PAI activity in healthy New Zealand White rabbits. As shown in FIG. 11, the infusion of Ang II was associated with a dose-dependent increase in mean blood pressure, while the animals that received Ang IV exhibited a stable mean BP throughout the course of the experiment. In contrast with these divergent effects on blood pressure, both agents induced a dose-dependent increase in plasma PAI-1 levels (FIG. 12). Control animals that received an infusion of normal saline showed no changes in BP or plasma PAI-1, while animals that received Ang II after pretreatment with amastatin (a synthetic inhibitor of the aminopeptidase that is responsible for the conversion of Ang III to Ang IV) exhibited the expected increases in blood pressure while the PAI-1 response was reduced considerably. These data add further evidence that Ang IV is responsible for the induction of endothelial PAI-1 production and secretion.

Other Examples—Method of In Vitro Testing of Angiotensin IV Antagonists

A variety of compounds are suitable for administration in the methods of the invention. These compounds will each have angiotensin IV agonistic or antagonistic activity. Methods of screening these compounds are presented below.

Northern blotting studies:

Cultured endothelial cells are exposed to Ang IV in the presence and absence of antagonists. After a several hour incubation period, cells are lysed and total RNA is isolated, gel electrophoresed, and transferred to a nylon membrane. The relative expression of PAI-1 mRNA is determined by hybridizing the membranes with $^{32}$P-labeled cDNA probes specific for PAI-1. Results are quantified by autoradiographyo Potency of Ang IV antagonism is inversely proportional to induction of PAI-1 message.

Protein secretion:

Cultured endothelial cells are exposed to Ang IV in the presence or absence of antagonists, After a 24 hour incubation period, the conditioned media is removed, centrifuged, and aliquots of the supernatant are assayed for the presence of PAI-1 antigen using a specific enzyme-linked immunosorbent assay (ELISA) for PAI-1.

Method of In Vivo Testing of Angiotensin IV Antagonists

New Zealand White rabbits are injected with graded doses of Ang IV. Simultaneously, they receive intravenous infusion of an ANG IV antagonist. Venous blood samples are collected during the infusions and assayed for PAI-1 antigen using a specific ELISA. Effective antagonists will blunt the secretion of PAI-1 into plasma.

What is claimed is:

1. An in vitro method of evaluating whether a compound will promote fibrinolysis, comprising:
   (a) providing cells having a receptor which specifically binds angiotensin IV and which are capable of expressing plasminogen activator inhibitor-1 (PAI-1) in the presence of angiotensin IV; and
   (b) contacting the cells with a mixture comprising angiotensin IV or an agonist of angiotensin IV and the compound to specifically bind said receptor; and
   (c) detecting the expression of PAI-1 to determine whether the compound induces substantial expression of PAI-1; and
   (d) selecting the compound as promoting fibrinolysis if it does not induce substantial expression of PAI-1.

2. The method of claim 1 wherein said cells are cultured endothelial cells.

3. The method of claim 1 wherein the detection of PAI-1 is determined by determining PAI-1 mRNA in the cells.

4. The method of claim 1 wherein the detection of PAI-1 is determined by assaying directly for PAI-1.

5. An in vitro method of evaluating whether a compound will promote fibrinolysis, comprising:
   (a) providing cells having a receptor which specifically binds angiotensin IV and which are capable of expressing plasminogen activator inhibitor-1 (PAI-1) in the presence of angiotensin IV; and
   (b) contacting the cells with a mixture comprising angiotensin IV or an agonist of angiotensin IV and the compound to specifically bind said receptor; and
   (c) detecting the binding of angiotensin IV to said receptor to determine whether the compound reduces the amount of angiotensin IV binding to the receptor, relative to a control without the compound; and
   (d) detecting the expression of PAI-1 to determine whether the compound induces substantial expression of PAI-1; and
   (e) selecting the compound as promoting fibrinolysis if it reduces specific binding of angiotensin IV to the receptor and does not induce substantial expression of PAI-1.

6. The method of claim 5 wherein said cells are cultured endothelial cells.

7. The method of claim 5 wherein the detection of PAI-1 is determined by determining PAI-1 mRNA in the cells.

8. The method of claim 5 wherein the detection of PAI-1 is determined by assaying directly for PAI-1.

9. The method of claim 1 or claim 5 wherein the compound has the following formula, or is an acetate salt thereof (SEQ ID NO:1):

A-B-C-HIS-PRO-D where
A=SAR or VAL
B=TYR OR TRP
C=ILE or VAL and
D=ALA or PHE;

provided that if A is VAL and B is TYR and C is ILE, then D is ALA.

* * * * *

SEQUENCE LISTING ( 1 ) GENERAL INFORMATION:

( i i i ) NUMBER OF SEQUENCES: 11

( 2 ) INFORMATION FOR SEQ ID NO: 1:

( i ) SEQUENCE CHARACTERISTICS:
        ( A ) LENGTH: 6
        ( B ) TYPE: amino acid
        ( C ) STRANDEDNESS: Not Relevant
        ( D ) TOPOLOGY: linear     ( i x ) FEATURE:
        ( D ) OTHER INFORMATION: Xaa in position 1 could be Sar
        or Val; Xaa in position 2 could be Tyr or Trp; Xaa in
        position 3 could be Ile or Val; Xaa in position 6 could
        be Ala or Phe.

( x i ) SEQUENCE DESCRIPTION: SEQ ID NO: 1:

Xaa Xaa Xaa His Pro Xaa
1               5

( 2 ) INFORMATION FOR SEQ ID NO: 2:

( i ) SEQUENCE CHARACTERISTICS:
        ( A ) LENGTH: 6
        ( B ) TYPE: amino acid
        ( C ) STRANDEDNESS: Not Relevant
        ( D ) TOPOLOGY: linear     ( x i ) SEQUENCE DESCRIPTION: SEQ ID NO: 2:

Val Tyr Ile His Pro Ala
1               5

( 2 ) INFORMATION FOR SEQ ID NO: 3:

( i ) SEQUENCE CHARACTERISTICS:
        ( A ) LENGTH: 6
        ( B ) TYPE: amino acid
        ( C ) STRANDEDNESS: Not Relevant
        ( D ) TOPOLOGY: linear     ( i x ) FEATURE:
        ( D ) OTHER INFORMATION: Xaa in position 1 could be Sar     ( x i ) SEQUENCE DESCRIPTION: SEQ ID NO: 3:

Xaa Tyr Ile His Pro Ala
1               5

( 2 ) INFORMATION FOR SEQ ID NO: 4:

( i ) SEQUENCE CHARACTERISTICS:
        ( A ) LENGTH: 6
        ( B ) TYPE: amino acid
        ( C ) STRANDEDNESS: Not Relevant
        ( D ) TOPOLOGY: linear     ( i x ) FEATURE:
        ( D ) OTHER INFORMATION: Xaa in position 1 could be Sar     ( x i ) SEQUENCE DESCRIPTION: SEQ ID NO: 4:

Xaa Tyr Val His Pro Ala
1               5

( 2 ) INFORMATION FOR SEQ ID NO: 5:

( i ) SEQUENCE CHARACTERISTICS:
        ( A ) LENGTH: 6

(B) TYPE: amino acid
(C) STRANDEDNESS: Not Relevant
(D) TOPOLOGY: Not Relevant (xi) SEQUENCE DESCRIPTION: SEQ ID NO: 5:

Val Trp Ile His Pro Ala
1               5

(2) INFORMATION FOR SEQ ID NO: 6:

(i) SEQUENCE CHARACTERISTICS:
(A) LENGTH: 6
(B) TYPE: amino acid
(C) STRANDEDNESS: Not Relevant
(D) TOPOLOGY: linear (xi) SEQUENCE DESCRIPTION: SEQ ID NO: 6:

Val Trp Val His Pro Ala
1               5

(2) INFORMATION FOR SEQ ID NO: 7:

(i) SEQUENCE CHARACTERISTICS:
(A) LENGTH: 6
(B) TYPE: amino acid
(C) STRANDEDNESS: Not Relevant
(D) TOPOLOGY: linear (ix) FEATURE:
(D) OTHER INFORMATION: Xaa in position 1 could be Sar (xi) SEQUENCE DESCRIPTION: SEQ ID NO: 7:

Xaa Trp Val His Pro Ala
1               5

(2) INFORMATION FOR SEQ ID NO: 8:

(i) SEQUENCE CHARACTERISTICS:
(A) LENGTH: 6
(B) TYPE: amino acid
(C) STRANDEDNESS: Not Relevant
(D) TOPOLOGY: linear (ix) FEATURE:
(D) OTHER INFORMATION: Xaa in position 1 could be Sar (xi) SEQUENCE DESCRIPTION: SEQ ID NO: 8:

Xaa Tyr Val His Pro Phe
1               5

(2) INFORMATION FOR SEQ ID NO: 9:

(i) SEQUENCE CHARACTERISTICS:
(A) LENGTH: 6
(B) TYPE: amino acid
(C) STRANDEDNESS: Not Relevant
(D) TOPOLOGY: linear (ix) FEATURE:
(D) OTHER INFORMATION: Xaa in position 1 could be Sar (xi) SEQUENCE DESCRIPTION: SEQ ID NO: 9:

Xaa Tyr Ile His Pro Phe
1               5

(2) INFORMATION FOR SEQ ID NO: 10:

(i) SEQUENCE CHARACTERISTICS:
(A) LENGTH: 6
(B) TYPE: amino acid ( C ) STRANDEDNESS: Not Relevant
( D ) TOPOLOGY: linear ( i x ) FEATURE:
( D ) OTHER INFORMATION: Xaa in position 1 could be Sar ( x i ) SEQUENCE DESCRIPTION: SEQ ID NO: 10:

Xaa Trp Val His Pro Phe
1               5

( 2 ) INFORMATION FOR SEQ ID NO: 11:

( i ) SEQUENCE CHARACTERISTICS:
( A ) LENGTH: 6
( B ) TYPE: amino acid
( C ) STRANDEDNESS: Not Relevant
( D ) TOPOLOGY: linear ( i x ) FEATURE:
( D ) OTHER INFORMATION: Xaa in position 1 could be Sar ( x i ) SEQUENCE DESCRIPTION: SEQ ID NO: 11:

Xaa Trp Ile His Pro Phe
1               5